United States Patent
Wei

(10) Patent No.: US 10,779,829 B2
(45) Date of Patent: Sep. 22, 2020

(54) TISSUE COMPRESSION DEVICE FOR CARDIAC VALVE REPAIR

(71) Applicant: EVALVE, INC., Santa Clara, CA (US)

(72) Inventor: Michael F. Wei, Redwood City, CA (US)

(73) Assignee: EVALVE, INC., Santa Clara, CA (US)

(*) Notice: Subject to any disclaimer, the term of this patent is extended or adjusted under 35 U.S.C. 154(b) by 123 days.

(21) Appl. No.: 15/616,723

(22) Filed: Jun. 7, 2017

(65) Prior Publication Data
US 2018/0353181 A1  Dec. 13, 2018

(51) Int. Cl.
*A61B 17/08* (2006.01)
*A61F 2/24* (2006.01)
(Continued)

(52) U.S. Cl.
CPC ...... *A61B 17/083* (2013.01); *A61B 17/00234* (2013.01); *A61B 17/10* (2013.01); *A61B 17/1227* (2013.01); *A61B 17/1285* (2013.01); *A61F 2/246* (2013.01); *A61F 2/2463* (2013.01); *A61F 2/2466* (2013.01); *A61B 2017/00243* (2013.01); *A61B 2017/00477* (2013.01); *A61B 2017/00783* (2013.01); *A61B 2090/061* (2016.02); *A61F 2230/0045* (2013.01);
(Continued)

(58) Field of Classification Search
CPC ....... A61B 17/08; A61B 17/083; A61B 17/10; A61B 17/105; A61B 17/122; A61B 17/1227; A61B 17/11; A61B 17/1285; A61B 2017/081; A61B 2017/1107; A61B 2017/1103; A61B 1/7128; A61B 17/0057; A61B 2017/0641; A61B 2017/00575; A61B 2017/00579; A61B 2017/00584; A61B 2017/00588; A61B 2017/00592; A61B 2017/00597; A61B 2017/00601; A61B 2017/0061; A61B 2017/00615; A61B 2017/00619; A61B 2017/00628; A61B 2017/00632; A61B 2017/00637; A61B 2017/00641; A61B 2017/00668; A61B 2017/00783; A61F 2/2463; A61F 5/0086; A61F 2/2487; A61F 2/2478
See application file for complete search history.

(56) References Cited

U.S. PATENT DOCUMENTS 9,414,825 B2 * 8/2016 Takahashi .......... A61B 17/0057
2004/0220593 A1 * 11/2004 Greenhalgh .......... A61F 2/2454
606/151
(Continued)

FOREIGN PATENT DOCUMENTS

WO    WO-2016110760 A1 *  7/2016  ......... A61B 17/0643

OTHER PUBLICATIONS

U.S. Appl. No. 15/616,727, filed Jun. 7, 2017, Wei.

*Primary Examiner* — Katherine H Schwiker
(74) *Attorney, Agent, or Firm* — Baker Botts L.L.P.

(57) ABSTRACT

The present disclosure describes interventional devices, systems, and methods for closing a regurgitant gap in a cardiac valve. Interventional devices are configured to be deployed between two previously placed implants or between a previously placed implant and a valve commissure. The interventional devices compress captured leaflet tissue and/or apply a tensioning force along the line of coaptation to assist in closing the gap and reducing regurgitant flow through the gap.

17 Claims, 13 Drawing Sheets

(51) Int. Cl.
    *A61B 17/128*     (2006.01)
    *A61B 17/122*     (2006.01)
    *A61B 17/00*     (2006.01)
    *A61B 17/10*     (2006.01)
    *A61B 90/00*     (2016.01)

(52) U.S. Cl.
    CPC ............... *A61F 2230/0054* (2013.01); *A61F 2230/0091* (2013.01)

(56) References Cited

U.S. PATENT DOCUMENTS

| | | | |
|---|---|---|---|
| 2005/0267529 A1* | 12/2005 | Crockett | A61B 17/083 606/215 |
| 2006/0229708 A1* | 10/2006 | Powell | A61F 2/2457 623/1.24 |
| 2008/0319475 A1* | 12/2008 | Clark | A61B 17/0057 606/213 |
| 2010/0010511 A1* | 1/2010 | Harris | A61B 17/083 606/143 |
| 2010/0016883 A1* | 1/2010 | Christoudias | A61B 17/29 606/205 |
| 2011/0077668 A1* | 3/2011 | Gordon | A61B 17/0057 606/142 |
| 2012/0245605 A1* | 9/2012 | Nicholson, IV | A61B 17/08 606/151 |
| 2013/0172914 A1* | 7/2013 | Weisshaupt | A61B 17/1227 606/151 |
| 2015/0057704 A1* | 2/2015 | Takahashi | A61B 17/0057 606/221 |

\* cited by examiner

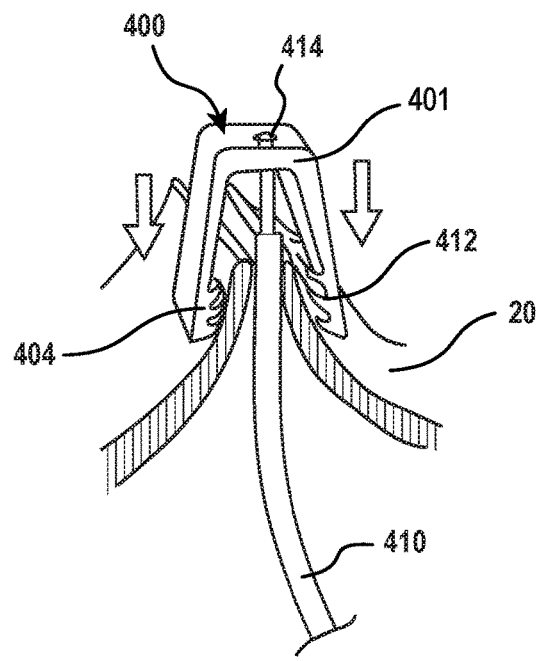
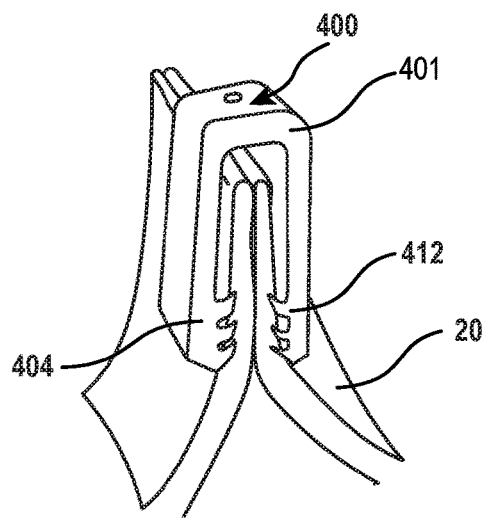
FIG. 7A    FIG. 7B
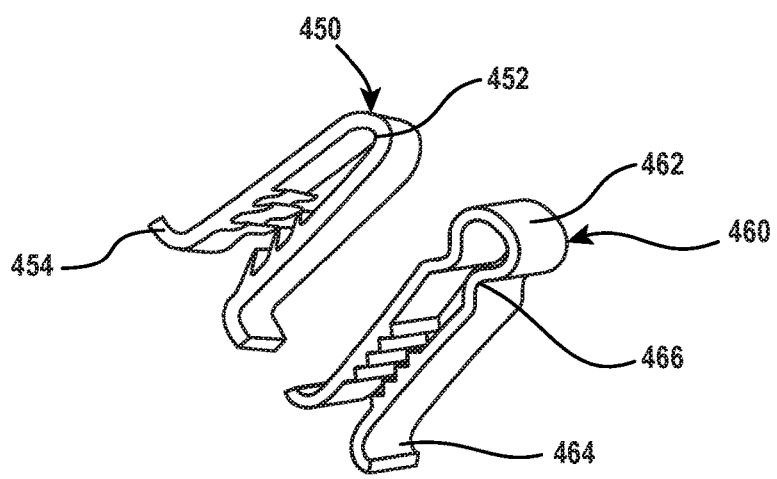
FIG. 8

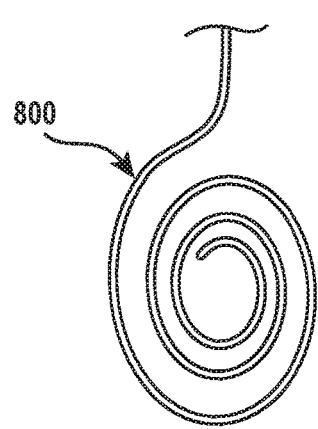 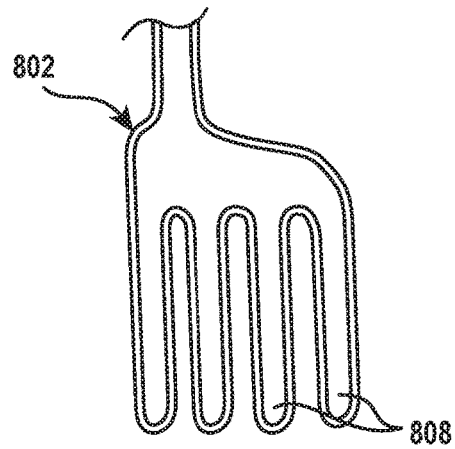 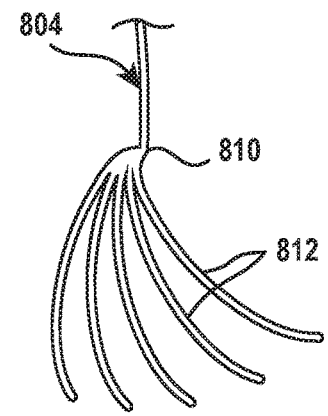
FIG. 13A   FIG. 13B   FIG. 13C
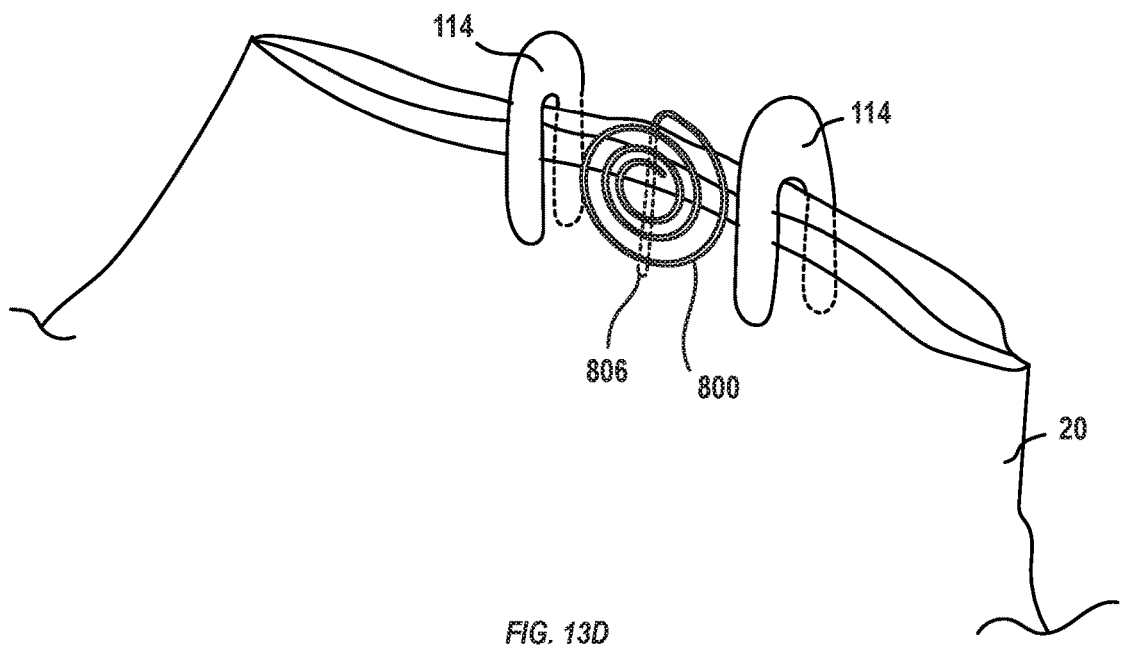
FIG. 13D

TISSUE COMPRESSION DEVICE FOR CARDIAC VALVE REPAIR

BACKGROUND

The mitral valve controls blood flow from the left atrium to the left ventricle of the heart, preventing blood from flowing backwards from the left ventricle into the left atrium so that it is instead forced through the aorta for distribution throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

Mitral valve regurgitation has several causes. Functional mitral valve regurgitation (FMR) is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues. In some circumstances, mitral valve regurgitation is a result of infective endocarditis, blunt chest trauma, rheumatic fever, Marfan syndrome, carcinoid syndrome, or congenital defects to the structure of the heart. Other cardiac valves, in particular the tricuspid valve, can similarly fail to properly close, resulting in undesirable regurgitation.

Heart valve regurgitation is often treated by repairing the faulty valve through an interventional procedure. In some circumstances, adjacent leaflets of the faulty valve are grasped and brought together using an interventional clip. The interventional clip is intended to remain deployed at the repaired valve to promote better coaptation of the grasped leaflets and to thereby reduce regurgitant flow through the valve. Although such a procedure may be beneficial, residual regurgitation can sometimes remain. A need therefore exists for solutions which further improve cardiac valve repair and associated patient outcomes.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure is directed to devices, systems, and methods for treating regurgitant leaks in cardiac valve tissue, including leaks along the cardiac valve line of coaptation. In some implementations, interventional device embodiments described herein may be deployed at gaps disposed between two previously deployed implants, or between a previously deployed implant and a valve commissure.

In one embodiment, an interventional device for compressing cardiac valve tissue at a targeted gap includes a distal member and a pair of opposing arms flexibly joined to the distal member. Each arm extends proximally from the distal member to a free end. The pair of opposing arms define an interior space between the arms for holding cardiac valve tissue. The arms have a default position and are flexibly moveable apart from one another away from the default position to increase the size of the interior space and to enable grasping of cardiac valve tissue within the interior space. The arms are configured to be biased toward the default position when moved apart from one another. In this manner, the arms provide a compressive force upon cardiac valve tissue held within the interior space.

In some embodiments, the interventional device is configured in size and shape for deployment at a targeted gap measuring about 2 mm to about 8 mm, or about 2 mm to about 5 mm. The interventional device may therefore be used in anatomical locations and/or under circumstances where deployment of a conventional clip (typically measuring 15 mm in length and 5 mm in width when closed) is improper. For example, an interventional device as described herein may be deployed between two conventional clips or between a conventional clip and a valve commissure. Such gaps may not provide sufficient space for deployment of another conventional clip, or may not provide sufficient space for the required articulation and maneuvering of a conventional clip.

In some embodiments, one or both of the free ends may flare outwardly. Some embodiments include an attachment point at the distal member for attaching to a delivery device. In some embodiments, one or both of the arms include a force-distributing pattern. In some embodiments, the device is formed from a shape-memory material such that the free ends, when deployed distally, sweep around proximally to grasp targeted cardiac valve tissue.

Some embodiments include an anchor configured to couple to the distal member. The anchor extends through the interior space and has a width greater than the distal member or the arms. The anchor may be positioned on the atrial side of a targeted cardiac valve while the distal member and arms are positioned on the ventricular side of the targeted valve. The anchor may include a textured surface for encouraging tissue ingrowth. The anchor may have a width of about 5 mm to about 8 mm.

In one embodiment, the interventional device includes a first arm which extends proximally from the distal member to form an inner member, and a second arm which extends proximally from the distal member and loops back distally to form a pair of outer members. The inner member is laterally offset from each of the outer members to avoid compressing tissue directly between any two of the arm members.

The interventional device may be deployed using a self-centering delivery catheter. The self-centering delivery catheter includes a pair of laterally extending fins extending from a distal section of the delivery catheter. The fins are configured to enable alignment of the delivery catheter with a line of coaptation at the targeted gap. In some embodiments, the self-centering delivery catheter is intra-procedurally adjustable in width. In one embodiment, the self-centering delivery catheter includes a pair of skives and a corresponding pair of wires laterally extendable through the skives to form the fins. The wires may extend through a lumen of the delivery catheter such that width of the fins is controllable via translation of the wires within the lumen.

One embodiment is directed to a method of reducing regurgitation through a cardiac valve by compressing leaflet tissue at a targeted gap of the cardiac valve. The method includes the steps of delivering an interventional tissue compression device to the targeted gap, and deploying the compression device at the targeted gap to compress the leaflet tissue and reduce regurgitant flow through the targeted gap. The targeted gap may be located at a mitral valve. The compression device may be delivered to the ventricular side of the mitral valve, then retracted proximally to enable the arms to grasp the leaflet tissue at the ventricular side of the mitral valve.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which:

FIGS. 7A and 7B illustrate deployment of a tissue compression device configured to grasp leaflet tissue at a targeted gap on the ventricular side of the mitral valve and to compress the tissue to aid in closing the gap;

FIG. 8 illustrates alternative embodiments of tissue compression devices;

FIGS. 13A through 13D illustrate various embodiments of a force-distributing feature which may be utilized at portions of a tissue tensioning and/or compression device;

DETAILED DESCRIPTION

Introduction

The present disclosure is directed to devices, systems, and methods for treating regurgitant leaks in cardiac valve tissue, including leaks along the cardiac valve line of coaptation. In some implementations, interventional device embodiments described herein may be deployed at gaps disposed between two previously deployed implants, or between a previously deployed implant and a valve commissure. The interventional devices may be deployed to apply a tensioning force along the line of coaptation and/or to compress captured leaflet tissue along a line orthogonal to the line of coaptation to assist in closing a targeted gap and reducing regurgitant flow through the gap.

Throughout this disclosure, many examples are described in the context of guiding a delivery system to a mitral valve. One of skill in the art will understand, however, that the described components, features, and principles may also be utilized in other applications. For example, at least some of the embodiments described herein may be utilized for guiding a delivery system to a pulmonary, aortic, or tricuspid valve.

Delivery System Overview

Figure 1:
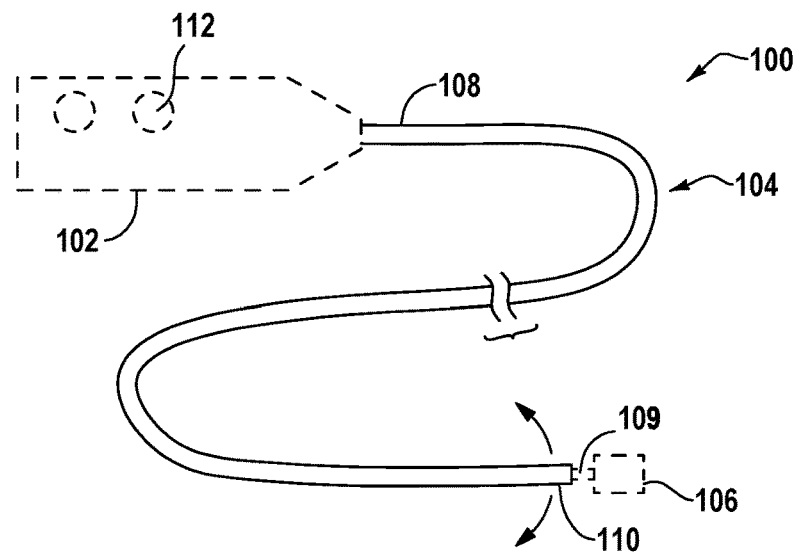
FIG. 1 illustrates an embodiment of a delivery system which may be utilized to deliver an interventional device to a targeted cardiac valve.

FIG. 1 illustrates a delivery system 100 which may be utilized to deliver an interventional device to a targeted cardiac valve. The illustrated delivery system 100 includes a handle 102 and a guide catheter 104 coupled to the handle 102. The handle 102 is connected to the proximal end 108 of the guide catheter 104 and may be configured to be operatively connected to one or more lumens of the guide catheter 104 to provide steering control over the guide catheter 104.

An interventional device 106 may be passable through an inner lumen of the guide catheter 104 to the distal end 110. The interventional device 106 generically represents any of the tensioning devices and/or compression devices described herein, such as those illustrated in FIGS. 5A through 13D. The interventional device 106 may be attached to a suitable delivery member 109 (e.g., delivery catheter, sheath, and/or push rod such as those illustrated in FIGS. 14 through 16C) for delivery through the guide catheter 104. One or more controls 112 may be included at the handle 102. The one or more controls 112 may be operatively coupled to the guide catheter 104 to provide steering control (e.g., by tensioning one or more control wires).

Figure 2:
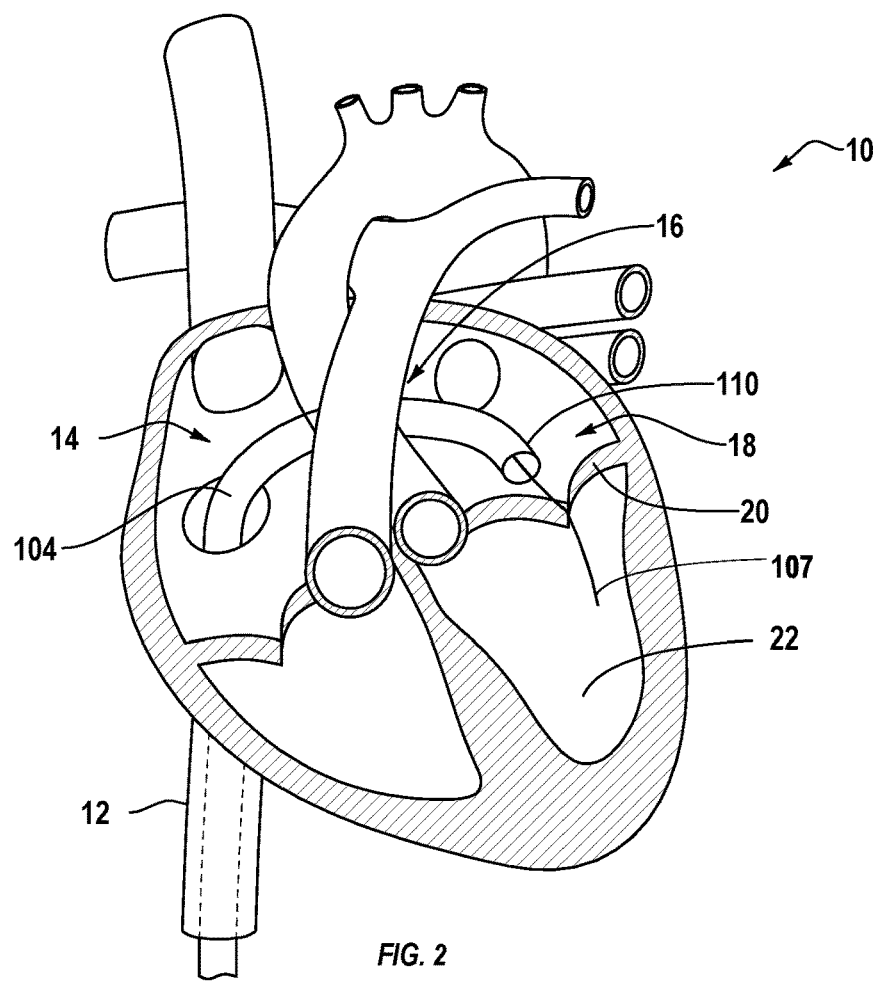
FIG. 2 illustrates a human heart and shows an exemplary intravascular approach by which a guide catheter of the delivery system of FIG. 1 may be routed to the heart to deploy the interventional device.

FIG. 2 illustrates a schematic representation of a patient's heart and a delivery procedure that may be conducted using the illustrated delivery system 100. The guide catheter 104 may be inserted into the patient's vasculature and directed to the inferior vena cava 12. The guide catheter 104 is passed through the inferior vena cava 12 toward the heart. Upon entering the heart from the inferior vena cava 12, the guide catheter 104 enters the right atrium 14. For procedures associated with repair of the mitral valve 20, the guide catheter 104 must further pass into the left atrium 18. As shown, the guide catheter 104 may reach the left atrium 18 through a puncture in the intra-atrial septum 16.

In other implementations, such as for procedures associated with a tricuspid valve, the guide catheter 104 may be passed through the inferior vena cava 12 into the right atrium 14, where it may then be positioned and used to perform the procedure related to the tricuspid valve. As described above, although many of the examples described herein are directed to the mitral valve, one or more embodiments may be utilized in other cardiac procedures, including those involving the tricuspid valve.

Although FIG. 2 and many of the other examples described herein illustrate a transfemoral approach for accessing a targeted cardiac valve, it will be understood that the embodiments described herein may also be utilized where alternative approaches are used. For example, embodiments described herein may be utilized in a transjugular approach, transapical approach, or other suitable approach. For repair procedures related to the mitral valve or tricuspid valve, delivery of the interventional device 106 is preferably carried out from an atrial aspect (i.e., with the distal end of the guide catheter 104 positioned within the atrium superior to the targeted valve). The illustrated embodiments are shown from such an atrial aspect. However, it will be understood that the interventional device embodiments described herein may also be delivered from a ventricular aspect.

In some embodiments, a guidewire 107 is utilized in conjunction with the guide catheter 104. For example, the guidewire 107 (e.g., 0.014 in, 0.018 in, 0.035 in) may be routed through the guide catheter 104 to the targeted cardiac valve. Once the guidewire has been properly positioned, the guide catheter 104 may be removed. The guidewire 107 may then remain in position so that one or more interventional devices 106 can travel over the guidewire to the targeted cardiac valve (e.g., via a suitable delivery catheter, sheath, and/or push rod).

Conventional Clip Deployment

Figure 3A:
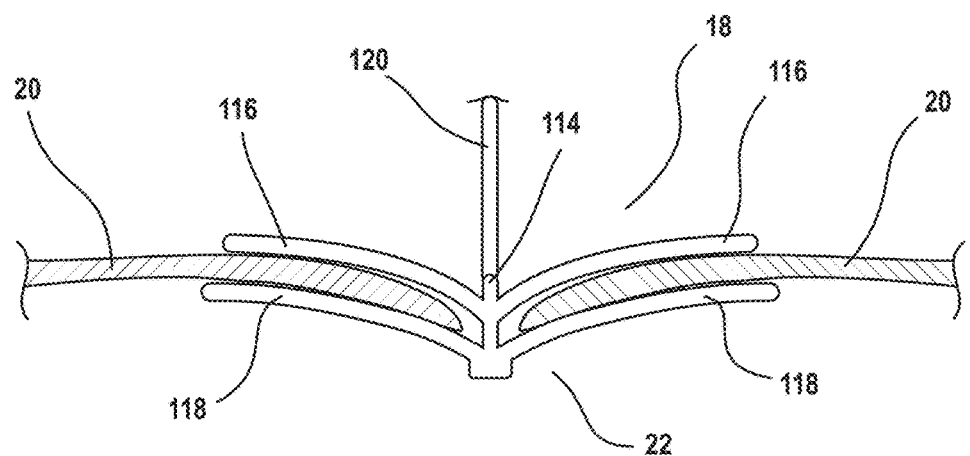
FIGS. 3A and 3B illustrate, in side view, deployment of a conventional clip device at a mitral valve.
Figure 3B:
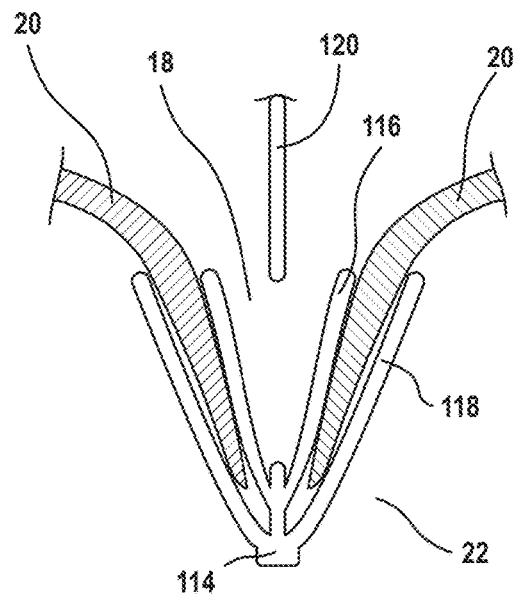

FIGS. 3A and 3B schematically illustrate, in side view, deployment of a conventional tissue clip 114 at the mitral valve 20. The clip 114 includes a pair of proximal arms 116 and an opposing pair of distal arms 118, with each proximal arm 116 corresponds to an opposing distal arm 118. The clip 114 configured so that an operator can control articulation of the arms to grasp leaflet tissue between the proximal arms 116 and distal arms 118, as shown. When the clip 114 is deployed and the leaflet tissue is grasped, the proximal arms 116 are positioned on the superior side of the valve leaflets (facing toward the left atrium 18) and the distal arms 118 are positioned on the inferior side of the valve leaflets (facing toward the left ventricle 22). Once the leaflet tissue has been sufficiently grasped, the clip 114 is moved to a closed, lower profile configuration, and the actuator rod 120 is detached and removed, as shown in FIG. 3B. The deployed and closed configuration is intended to affix the grasped leaflet tissue to promote improved leaflet coaptation and reduced regurgitation at the mitral valve 20.

An example of a conventional tissue clip 114 is the MitraClip® device available from Abbott Vascular. A typical clip 114 has a closed clip length of about 15 mm. The typical clip 114 has an open clip width of about 20 mm and a closed clip width of about 5 mm.

Figure 4:
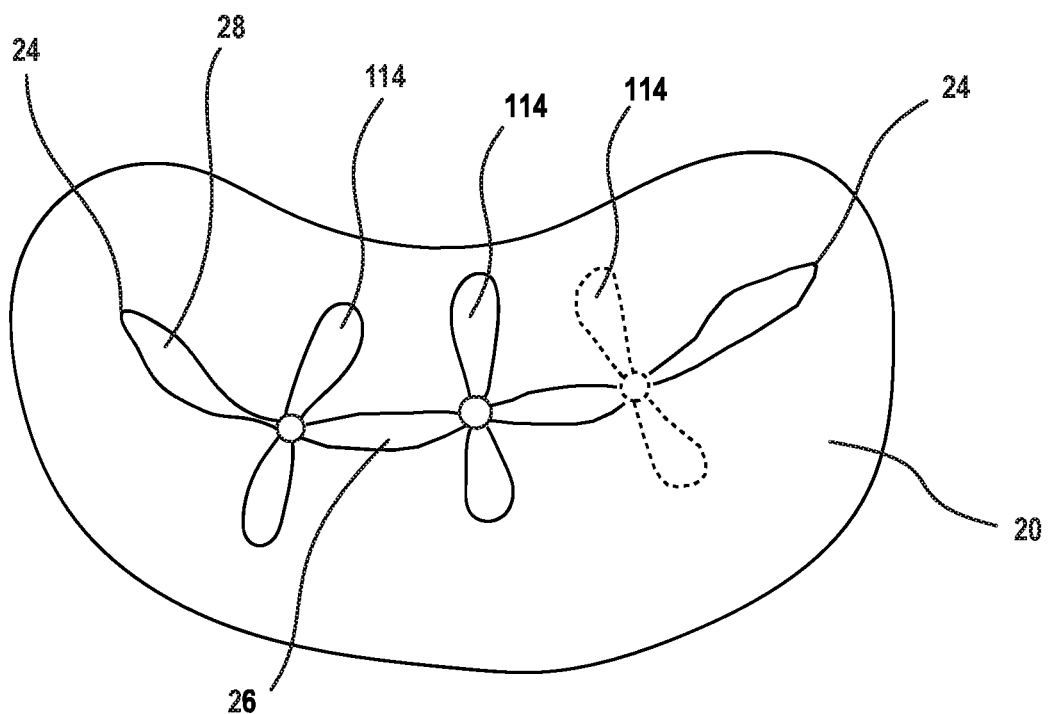
FIG. 4 illustrates a superior view of the mitral valve showing placement of conventional clip devices and showing gaps where residual regurgitation may occur.

FIG. 4 illustrates the mitral valve 20 from a superior aspect. As shown, a set of conventional clips 114 have been deployed and implanted at the mitral valve 20. In some circumstances, use of such conventional clips 114 does not completely reduce regurgitation through the mitral valve 20, and an amount of residual regurgitation remains. For example, residual regurgitation may occur at a gap 26 located between two implanted clips 114 and/or may occur at a gap 28 located between a commissure 24 and an implanted clip 114.

In some circumstances, it may not be clinically appropriate to deploy another such conventional clip 114 at a gap where residual regurgitation is occurring. For example, the targeted gap may be too small to fit another clip 114. Further, even if the targeted gap is large enough to fit another clip 114 in a closed and deployed position (e.g., with a closed clip width of about 5 mm), there may be insufficient space to safely maneuver, articulate, and deploy the clip 114 at the targeted gap without entangling nearby tissues, damaging clip components, and/or displacing a previously placed clip. In other circumstances, use of an additional clip 114 may be inappropriate because the clip 114 would grasp too much of the relatively narrow gap and would risk causing stenosis of the valve. In such circumstances, the residual regurgitation, while not ideal, is often allowed to continue because it is preferable to risking valve stenosis.

Accordingly, there are many situations in which valve leakage exists but conventional repair devices and procedures are inappropriate. The devices, systems, and methods described below may be utilized in such circumstances to provide effective reduction of regurgitation. Although many of the examples illustrated and described herein relate to deployment of an interventional device between two previously deployed tissue clips, it will be readily understood that the described features and components may be readily utilized in other applications where leakage occlusion is intended. For example, one or more of the embodiments described below may be utilized to treat a paravalvular leakage (e.g., in a mitral valve, aortic valve, or other cardiac valve), other vascular leakages, or to treat leakage between an implanted device and a naturally occurring structure, such as between an implanted device and a valve commissure.

Embodiments described below may be deployed to effectively treat gaps of about 1 mm to about 10 mm, or about 2 mm to about 8 mm. Included in the foregoing ranges, gaps of about 5 mm or less (e.g., about 2 mm to 5 mm) may be effectively treated using one or more of the embodiments described below. Further, although the examples shown below illustrate treatment of a single gap, it will be understood that in at least some applications, a plurality of gaps may be treated. For example, as shown by the dashed-line conventional clip 114 of FIG. 4, there may be circumstances where multiple treatable gaps exist, where one or more may be located between two implanted clips and one or more may be located between an implanted clip and a valve commissure.

Tissue Tensioning Devices

Figure 5A:
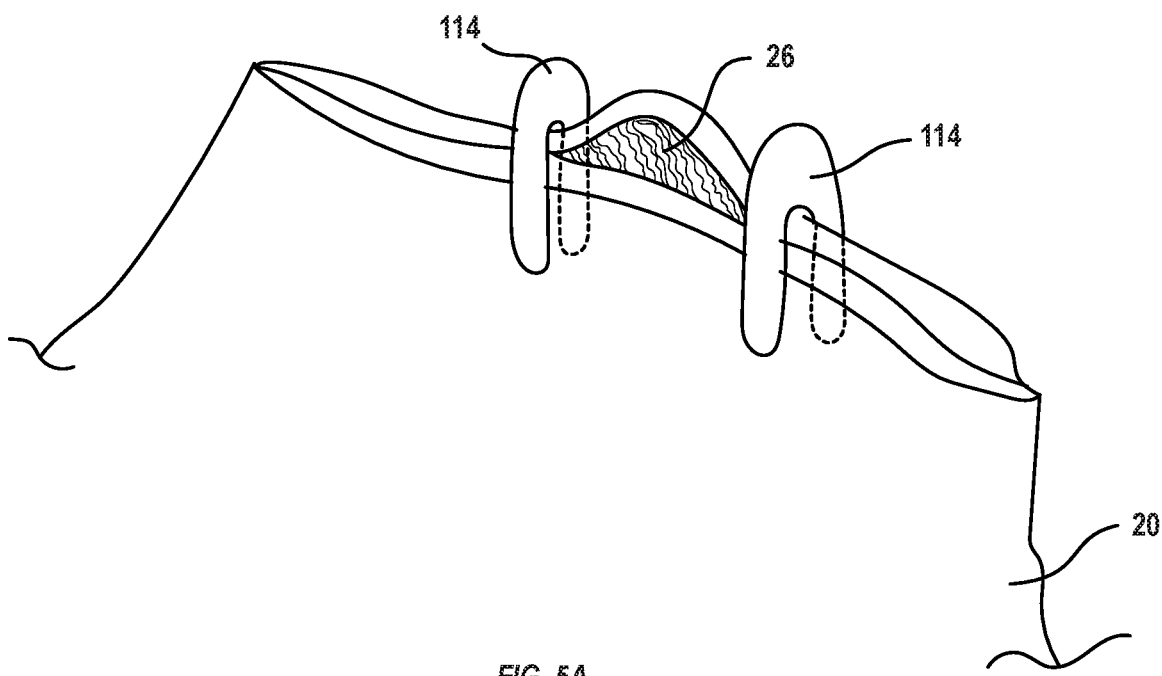
FIGS. 5A through 5C illustrate an embodiment of a tissue tensioning device configured to be positioned within a targeted gap and to tension leaflet tissue at the gap along the line of coaptation to aid in closing the gap.
Figure 5B:
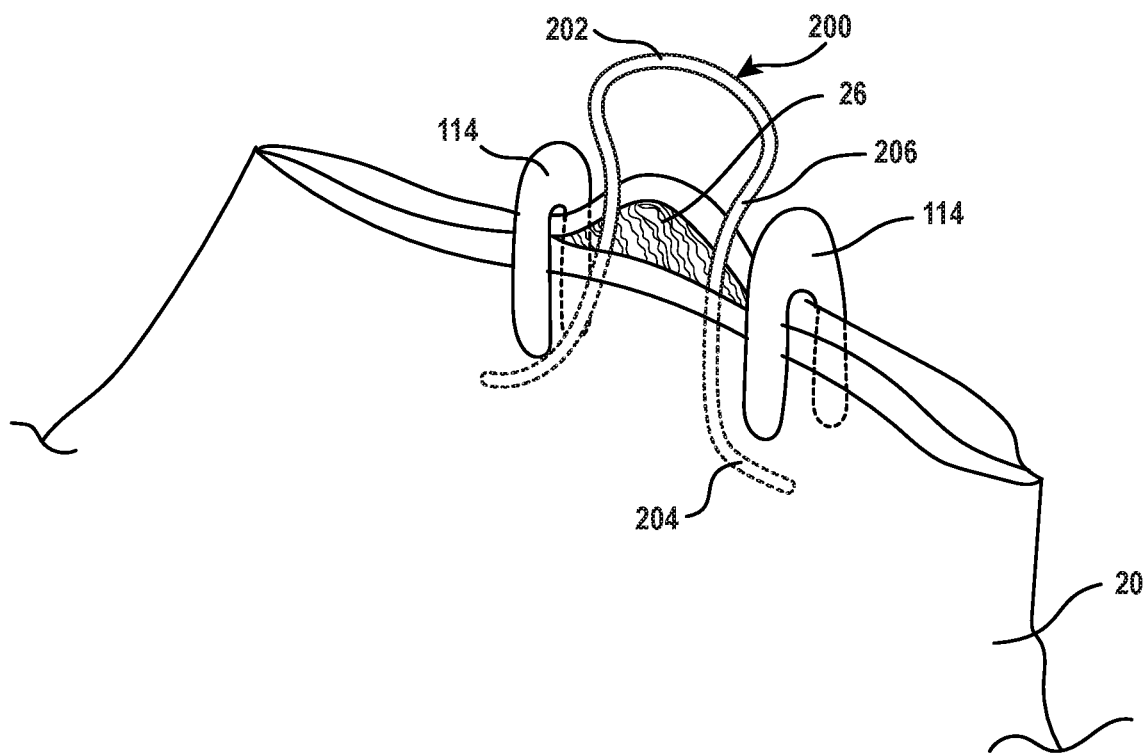
Figure 5C:
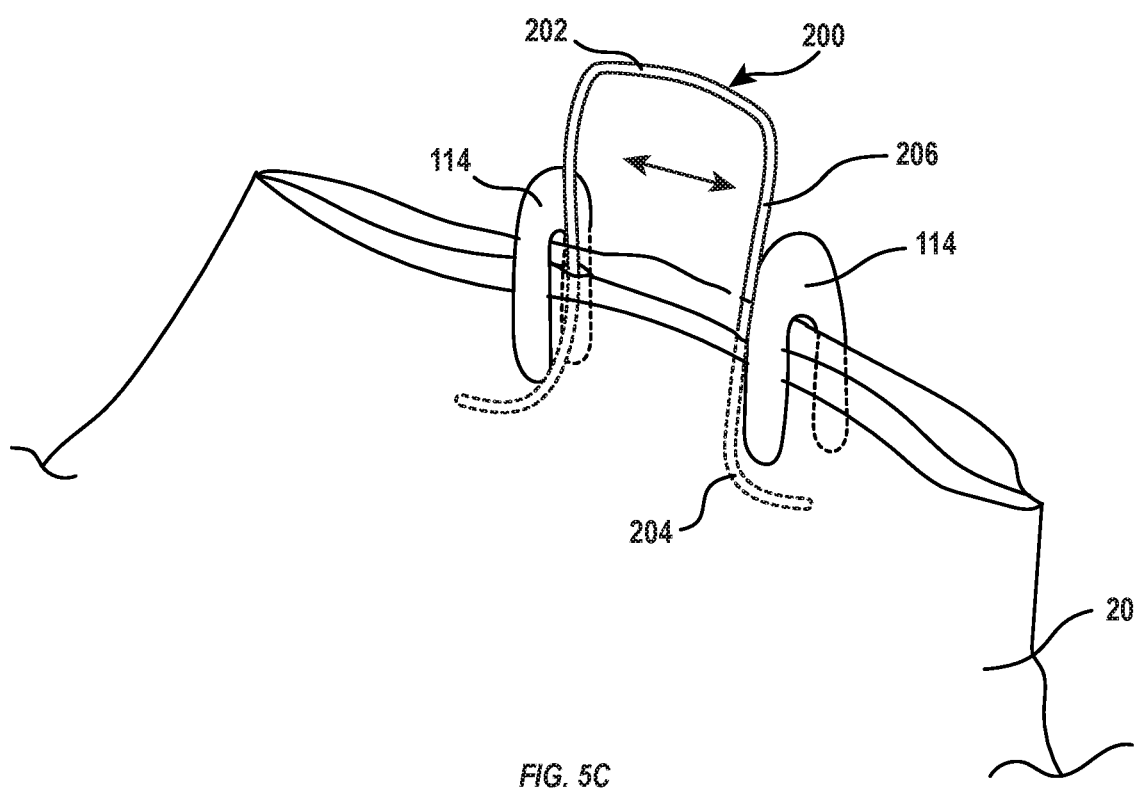

FIGS. 5A through 5C illustrate deployment of an interventional device configured as a tissue tensioning device 200 configured to apply a tensioning force along the line of coaptation of a targeted gap in a cardiac valve. The views of FIGS. 5A through 5C show the mitral valve 20 from the ventricular side. As shown in FIG. 5A, a gap 26 may exist between two clips 114 previously deployed at the mitral valve 20. FIG. 5B shows insertion of the tensioning device 200 within the targeted gap 26. The illustrated tensioning device 200 includes a distal section 202, an intermediate section 206, and a proximal section 204. In the illustrated embodiment, the tensioning device 200 is formed as wire having free ends at the proximal section 204 which extend to form opposing members of the intermediate section 206 before meeting and closing at the distal section 202.

The tensioning device 200 is configured so that at least the intermediate section 206 may be biased laterally outwardly. As shown in FIG. 5C, after positioning the tensioning device 200 within the gap 26, the intermediate section 206 is allowed to laterally expand along the line of coaptation. The laterally expanding structure of the intermediate section 206 abuts against the implanted clips 114 and forces them further away from one another to thereby assist in closing the gap 26.

The tensioning device 200 is preferably formed with a width that is allows the device to fit within the targeted gap and provide the laterally outward tensioning force. For example, the tensioning device 200 may have a default, expanded width of about 1 to 3 mm greater than the targeted gap. In this manner, the tensioning device 200 can be positioned within the gap in the laterally compressed state which provides the outward lateral tensioning force. The tensioning device 200 is preferably sized for deployment at a gap of approximately 1 to 10 mm, or about 2 to 8 mm in width, including relatively small gaps of about 2 to 5 mm in width. The length of the device may be up to about 9 mm, such as about 5 to 9 mm.

The tensioning device 200 may be deployed, for example, by routing a delivery catheter carrying the tensioning device 200 through the targeted gap 26 from the atrial side to the ventricular side, and unsheathing the tensioning device 200 to allow it to expand along the line of coaptation from the more compressed, smaller width profile shown in FIG. 5B to the expanded, larger width profile shown in FIG. 5C.

In the illustrated embodiment, the proximal section 204 of the tensioning device 200 includes free ends that extend or flare outwardly to provide a greater overall width to the proximal section 204 relative to the intermediate section 206. This feature may aid in preventing the tensioning device 200 from being forced distally through mitral valve 20 and carried downstream into the ventricle. The illustrated embodiment is configured with a closed distal section 202 and an open proximal section 204. The proximal section 204 may alternatively be closed in a manner similar to the distal section 202. In some embodiments, the proximal section 204 is closed and the distal section 202 is open. In each embodiment, however, it is preferred that at least the proximal section 204 have a width greater than the intermediate section 206.

The illustrated tensioning device 200 is shown as a simple wire structure. In other embodiments, the tensioning device may include an interior wireframe assembly, elastomer film cover, and/or other interior structural elements. The tensioning device 200 may be formed from any suitable biocompatible material, including biocompatible metals, alloys, polymers, and combinations thereof. In some embodiments, the tensioning device 200 is formed at least partially from a superelastic material such as nitinol. The tensioning device 200 may also be formed from a cobalt-chromium-nickel alloy (e.g., Elgiloy®), polypropylene, polyester, polylactide (e.g., PLLA or PLA), polyglycolide (PGA).

Figure 6A:
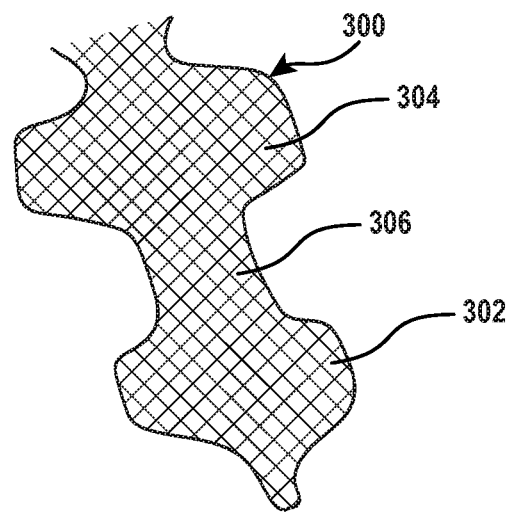
FIGS. 6A and 6B illustrate another embodiment of a tissue tensioning device.
Figure 6B:
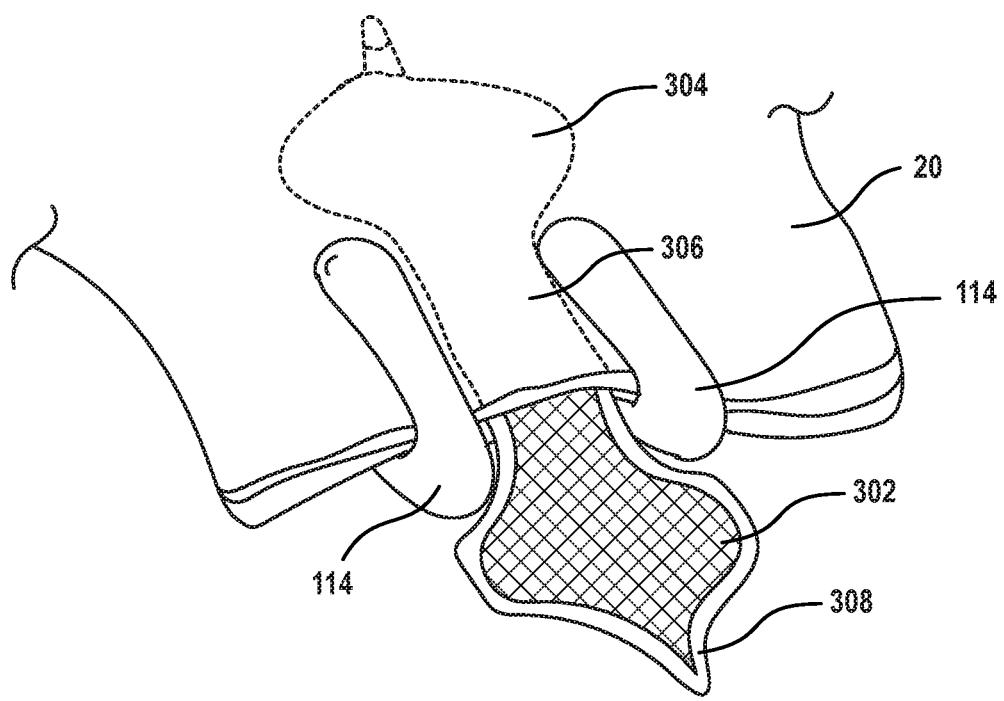

FIGS. 6A and 6B illustrate another embodiment of a tissue tensioning device 300 which may be delivered to a targeted gap to reduce regurgitation/leakage through the gap. FIG. 6A illustrates a perspective view of the tensioning device 300, and FIG. 6B illustrates the tensioning device 300 in a deployed position at the mitral valve 20. The tensioning device 300 may be configured in some aspects (e.g., materials, size) similar to tissue tensioning device 200 described above.

The illustrated tensioning device 300 includes a proximal section 304, an intermediate section 306, and a distal section 302. When deployed, the tensioning device 300 is positioned such that the distal section 302 extends through the mitral valve 20 and into the ventricle, while the proximal section 304 remains on the atrial side of the mitral valve 20. The intermediate section 306 is positioned at the gap between the implanted clips 114. In a manner similar to the tensioning device 200 of FIGS. 5B and 5C, the intermediate section 306 of the tensioning device 300 biases laterally outward along the line of coaptation and against the implanted clips 114 to assist in closing the gap between the implanted clips 114.

The illustrated tensioning device 300 may be deployed at the mitral valve 20 in a manner similar to the tensioning device 200 of FIGS. 5B and 5C. For example, the tensioning device 300 may be delivered to the mitral valve 20 in a sheathed, low profile configuration. The distal section 302 may be unsheathed first to open at the ventricular side of the targeted gap. Further unsheathing then exposes the intermediate section 306 and proximal section 304.

In the illustrated embodiment, the distal section 302 and the proximal section 304 are formed with deployed widths that are greater than the deployed width of the intermediate section 306. This substantially flat "hourglass" shape can beneficially prevent the tensioning device 300 from translating away from the valve 20 and embolizing downstream. The tensioning device 300 may be formed as a braided or mesh wire structure. In some embodiments, the perimeter 308 of the device is formed as a solid wire to which the interior wire mesh attaches.

The tensioning device may be formed using any suitable biocompatible material. The tensioning device 300 may also be formed from a cobalt-chromium-nickel alloy (e.g., Elgiloy®), polypropylene, polyester, polylactide (e.g., PLLA or PLA), polyglycolide (PGA), for example. In some embodiments, a nitinol wireframe structure is shape set in the desired flat hourglass shape to form the tensioning device 300. The interior mesh may provide a textured surface which beneficially encourages tissue ingrowth. Alternatively, the interior mesh may be omitted.

Tissue Compression Devices

FIGS. 7A and 7B illustrate an embodiment of a tissue compression device 400 which may be delivered to a targeted gap to reduce regurgitation/leakage through the gap. The tissue compression device 400 is configured to compress captured tissue along a line orthogonal to the line of coaptation of the targeted cardiac valve tissue. The illustrated compression device 400 includes a distal member 401 and a pair of opposing arms 404 that extend proximally from the distal member 401. The compression device 400 is configured to grasp and hold leaflet tissue within an interior space between the opposing arms 404. The compression device 400 may thereby aid in closing the gap and reducing regurgitation by compressing the grasped tissue. The illustrated compression device 400 also includes frictional elements 412 for improving the engagement of the arms 404 with the leaflet tissue. The compression device 400 is configured to provide sufficient compression of grasped tissue for a desired period of time to enable tissue bridging/fusion without overly compressing the tissue and causing necrosis or damage during delivery.

A delivery member 410 detachably couples to the distal member 401 at the attachment point 414. The compression device 400 may be deployed by passing the delivery member 410 through the mitral valve 20 from the atrial side (the bottom side in FIGS. 7A and 7B) to the ventricular side (the upper side in FIGS. 7A and 7B). The delivery member 410 may then be retracted proximally to bring the interior side of the arms 404 into engagement with the leaflet tissue on the ventricular side of the mitral valve 20, as shown in FIG. 7A. The delivery member 410 is then detached from the distal member 401 and removed, leaving the compression device 400 in place on the ventricular side of the mitral valve 20 with the leaflet tissue affixed between the opposing arms 404 as shown in FIG. 7B.

The illustrated compression device 400 is preferably formed from a flexible material capable of flexing sufficiently to allow the arms 404 to position over and grasp the leaflets. The flexible compression device 400 may therefore be deployed without requiring articulation of the arms 404 or relatively complex operator control over arm position relative to the valve 20. The illustrated compression device 400 is flexible such that when the arms 404 are moved apart and away from the default position—such as when they are positioned over the leaflet tissue—the arms 404 will be biased back toward the default position, in a direction orthogonal to the line of coaptation, to provide a compressive force upon the grasped leaflet tissue.

The compression device 400 may also be formed from a cobalt-chromium-nickel alloy (e.g., Elgiloy®), polypropylene, polyester, polylactide (e.g., PLLA or PLA), polyglycolide (PGA). In some embodiments, the compression device 400 is formed from a bioabsorbable material. Such embodiments may provide for natural tissue bridging and fusion at the targeted gap. The compression device 400 is preferably sized for deployment at a gap of approximately 1 to 10 mm, or about 2 to 8 mm in width. The compression device 400 may have a width of about 5 mm or less, such as about 2 to 5 mm. The length of the arms 404 may be up to about 9 mm, such as about 5 to 9 mm.

FIG. 8 illustrates alternative embodiments of tissue compression devices 450 and 460. The compression devices 450 and 460 (as well as the additional compression device embodiments described below) may be configured in some aspects (e.g., materials, size) similar to compression device 400 described above. As shown by compression device 450, the distal section 452 may be substantially rounded rather than angular. As shown by compression device 460, the distal section 462 may include a neck 466 configured to act as a flexible, living hinge from which the extending arms 464 can flex. Both the compression device 450 and the compression device 460 include arms 454 and 464 which flare outwardly at their proximal ends. The flared construction may assist in capturing leaflet edges and bringing leaflets into the interior space between the opposing arms as the device is retracted proximally over the leaflets.

Figure 9A:
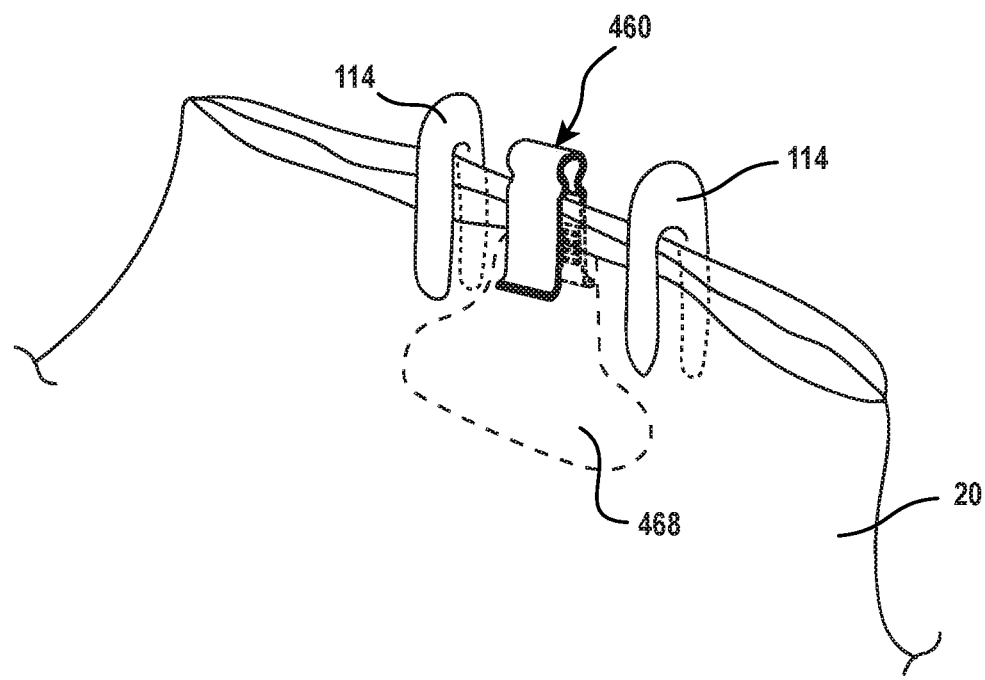
FIGS. 9A and 9B illustrate an embodiment of a tissue compression device having an attached anchor member configured for placement on the atrial side of the mitral valve to prevent displacement of the tissue compression device.
Figure 9B:
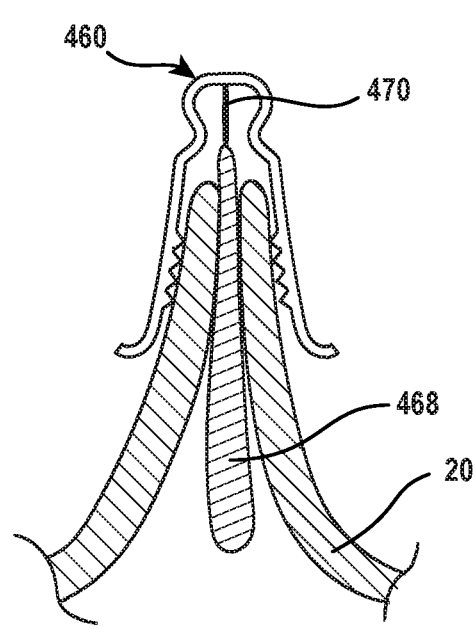

FIGS. 9A and 9B illustrate use of the compression device 460 in conjunction with an atrial anchor 468. FIG. 9A is a view from the ventricular side, while FIG. 9B is a cross-sectional side view. As shown in FIG. 9B, the atrial anchor 468 is attached to the compression device 460 at attachment point 470. The compression device 460 may be deployed on the ventricular side of the valve 20 in the manner described above with respect to compression device 460. The atrial anchor 468 is positioned on the atrial side, and is sized with a width that is greater than the width of the compression device 460 and preferably also exceeds the width of the gap so as to prevent movement of the atrial anchor 468 and attached compression device 460 downstream from the valve 20. The atrial anchor 468 may be formed from a mesh, latticed, or otherwise textured material that encourages ingrowth of the compressed leaflet tissue affixed against the atrial anchor 468.

The compression device 460 and the atrial anchor 468 may be delivered in one piece as an integral device. Alternatively, the compression device 460 and atrial anchor 468 may be delivered sequentially and then locked together at the attachment point 470. For example, the atrial anchor 468 may be unsheathed or otherwise delivered to the atrial side of the targeted gap. The compression device 460 may then be routed through the targeted gap to the ventricular side, then retracted back until mechanically engaged with the atrial anchor 468. In alternative embodiments, a suture or other suitable connection member may be used to connect the compression device 460 and atrial anchor 468. Although the particular compression device 460 is illustrated here, it will be understood that other compression device embodiments described herein may also be utilized with an atrial anchor in a similar manner.

Figure 10A:
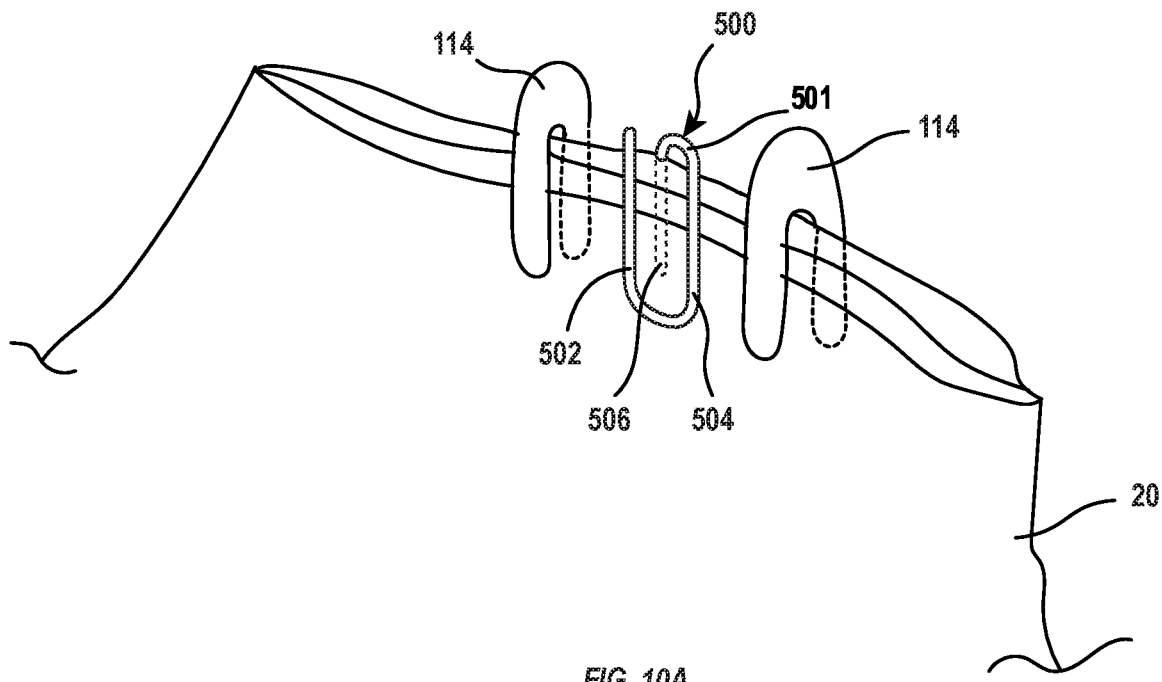
FIGS. 10A and 10B illustrate an embodiment of a tissue compression device formed with a clip-like construction and having an inner member offset from two outer members to avoid compressing leaflet tissue directly between two arm members.
Figure 10B:
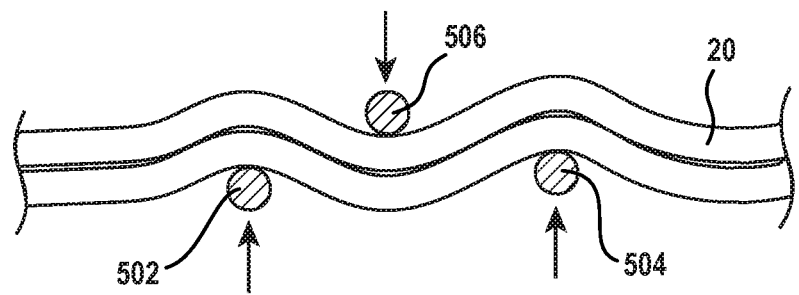

FIGS. 10A and 10B illustrate another embodiment of a tissue compression device 500 which may be delivered to a targeted gap to reduce regurgitation/leakage through the gap. FIG. 10A is a view of the mitral valve 20 from the ventricular side and FIG. 10B is a cross-sectional view taken along the line of coaptation. The compression device 500 includes a distal member 501 and two arms which extend proximally from the distal member 501. A first arm loops back distally to form two extended outer members 502 and 504. The second arm extends proximally to form an inner member 506. The inner member 506 extends between the outer members 502 and 504. The outer members 502 and 504 and the inner member 506 are connected in a clip configuration such that when deployed at the targeted gap, the outer members 502 and 504 may be positioned on one side of the captured leaflets while the inner member 506 is positioned on the opposite side of the captured leaflets.

As shown in FIG. 10B, the inner member 506 is laterally offset to extend between the outer members 502 and 504. With this configuration, when the compression device 500 is deployed, the captured leaflet tissue is not compressed directly between any two hard structures. The offset lines of compression may prevent over-compression of tissue to avoid injury and necrosis. Some embodiments may include barbs or other frictional elements (not shown) to promote engagement with captured tissue.

The compression device 500 may be delivered in a manner similar to the compression device 400 as described in relation to FIGS. 7A and 7B. For example, a delivery member may attach to the distal member 501. The compression device 500 may be delivered to the ventricular side of the valve 20, and then retracted proximally to bring the outer members 502 and 504 and inner member 506 into position on opposite sides of the grasped leaflets.

Figure 11A:
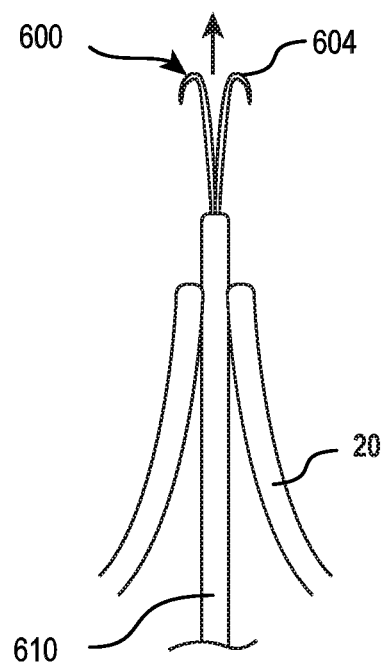
FIGS. 11A through 11C illustrate deployment of an embodiment of a tissue compression device having shape memory, showing initial distal deployment of the free ends of the device followed by the arms sweeping around and extending proximally to engage leaflet tissue.
Figure 11B:
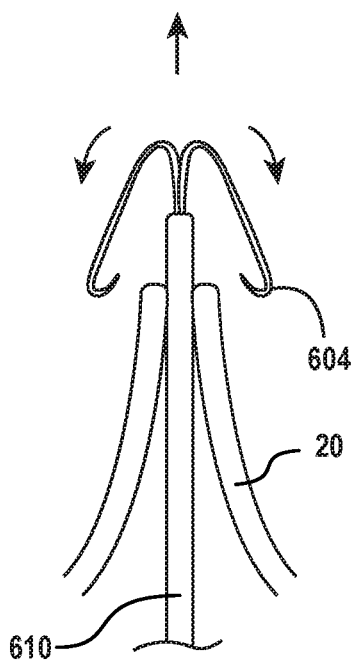
Figure 11C:
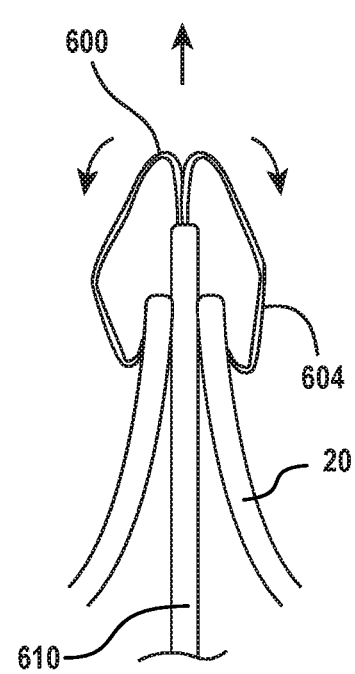

FIGS. 11A through 11C illustrate in cross-sectional side view an embodiment of a tissue compression device 600 having self-closing features. A delivery catheter 610 is shown with a distal end delivered through the mitral valve 20 to the ventricular side (the upper side in the Figures). The compression device 600 is unsheathed and deployed from the delivery catheter 610 with the proximal free ends 604 extending first out of the delivery catheter. An inner push rod (not shown), for example, may extend within the delivery catheter 610 to enable pushing of the compression device 600 distally out of the delivery catheter 610. As shown in FIG. 11B, further deployment of the compression device 600 out of the delivery catheter 610 allows the proximal free ends 604 to sweep laterally outwardly and rotate back toward the axis of the delivery catheter 610. As shown in FIG. 11C, further deployment allows the proximal free ends 604 to wrap around proximally on opposite sides of the leaflets of the mitral valve 20 and to engage with the outer surfaces of the leaflets. The compression device 600 may then be detached from the delivery catheter 610 and the delivery catheter 610 removed.

The compression device 600 is formed from a suitable shape memory material (e.g., nitinol) processed at a transition temperature to set the desired final deployed shape. The compression device 600 is preferably processed at a suitably low temperature to allow straightening and installation into the lower profile shape within the delivery catheter 610 without exceeding the strain properties and causing plastic deformation. Once exposed to the relatively elevated temperature within the body, the unsheathed or extruded device will progressively transition in shape to the final position capable of grasping leaflet tissue.

Combination Compression/Tensioning Devices

FIGS. 12A through 12D illustrate an exemplary embodiment of a device 700 configured to both tension and compress tissue at a targeted gap. As described below, the device 700, when deployed at a targeted gap of a cardiac valve, provides tension along the line of coaptation of the gap while simultaneously providing compression of grasped tissue along a line orthogonal to the line of coaptation.

Figure 12A:
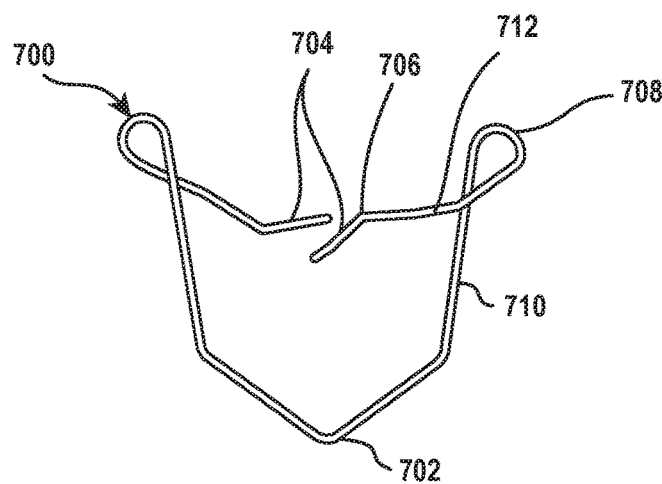
FIGS. 12A through 12D illustrate an embodiment of a combination tissue tensioning and tissue compression device configured to tension leaflet tissue along the line of coaptation and to compress leaflet tissue to aid in closing a targeted gap.

As shown in FIG. 12A, the combination device 700 includes a pair of free ends 704 which each angle at bend 706 and then extend as a lateral member 712. Each lateral member 712 then loops at bend 708 and extends as a longitudinal member 710. The opposing longitudinal members 710 meet and close at a proximal end 702. Although not shown, the combination device 700 may optionally include a mesh or webbing to encourage tissue ingrowth.

Figure 12B:
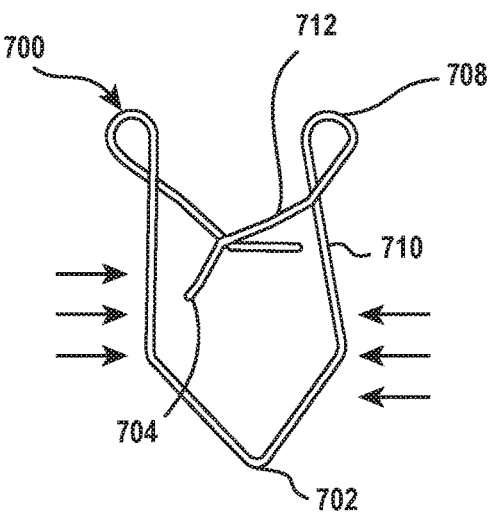

As shown in FIG. 12B, the combination device 700 may be flexed so that the longitudinal members 710 move inwardly and the overall width of the device 700 is reduced. From such a constrained position, the device will provide an outward lateral force toward the default, wider position shown in FIG. 12A.

Figure 12C:
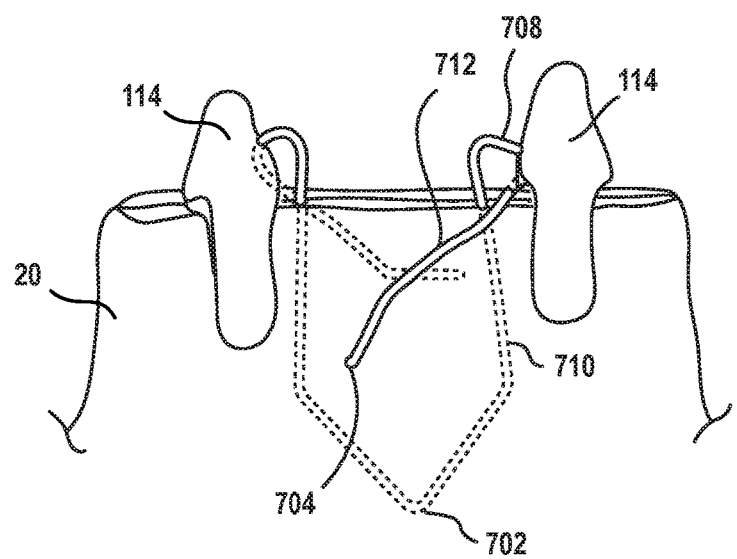
Figure 12D:
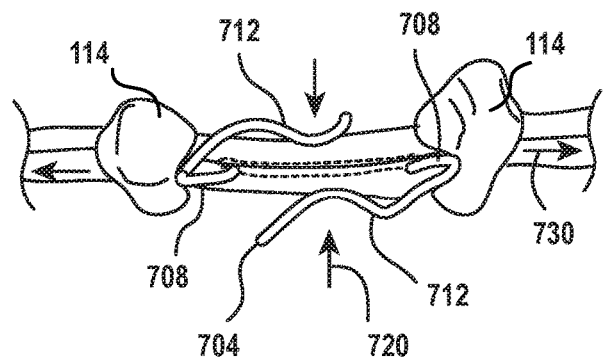

FIGS. 12C and 12D illustrate the combination device 700 in a deployed position at a targeted gap between two conventional clips 114. FIG. 12C is a side view showing the ventricular side of the valve 20 and FIG. 12D is a view from a position inferior to the valve 20. When positioned within the gap, the lateral outward tensioning force 730 provided by the opposing longitudinal members 710 can cause the device 700 to abut against and force the clips 114 apart from one another. This will bring leaflets of the gap into contact with one another to assist in closing the gap. In addition to the tensioning force 730, the combination device provides a compressive force 720 against the grasped leaflet tissue. The lateral members 712 are positioned on opposite sides of the grasped leaflets and are biased toward one another to compress the tissue held between.

The combination device 700 may be deployed in a manner similar to the deployment of compression device 600 shown and described in relation to FIGS. 11A through 11C. For example, the combination device 700 may be formed from a suitable shape memory material (e.g., nitinol) and deployed by unsheathing the device 700 at the targeted gap. The free ends 704 may be unsheathed first and allowed to sweep around on opposite sides of the leaflets to form the lateral members 712. The remainder of the device 700, including the longitudinal members 710 and proximal end 702, may then be unsheathed at the desired position within the targeted gap.

Force-Distributing Features

FIGS. 13A through 13D illustrate embodiments of tissue compression devices having force-distributing features.

FIGS. 13A through 13C show various exemplary wire patterns which may be utilized at one or more sections of a compression device to provide greater effective surface area. The relatively high effective surface area better distributes compressive forces upon the grasped tissue while also providing effective contact and tissue engagement. FIG. 13A illustrates a portion of a compression device 800 having a looping or spiraling pattern. FIG. 13B illustrates a portion of a compression device 802 having a serpentine or winding pattern of extensions 808. FIG. 13C illustrates a portion of a compression device 804 having a forked pattern with a plurality of extensions 812 radiating from a common point 810.

Force-distributing features such as those illustrated may be included with any of the compression or combination compression/tensioning devices described above. For example, any of the illustrated force distributing patterns, or combinations thereof, may be used at the free ends of the embodiments shown in FIGS. 10A through 12D.

FIG. 13D illustrates the compression device 800 as deployed at a targeted gap of the mitral valve 20. As shown, the force-distributing spiral pattern is employed on one side of the grasped tissue and an inner member 806 is disposed on the opposite side of the grasped tissue. The spiral pattern functions to distribute applied forces and prevent overly compressing tissue grasped between the spiral pattern and the inner member 806. Alternative embodiments may include one or more force-distributing features on both sides.

Self-Centering Delivery Catheter and Sizer

Figure 14:
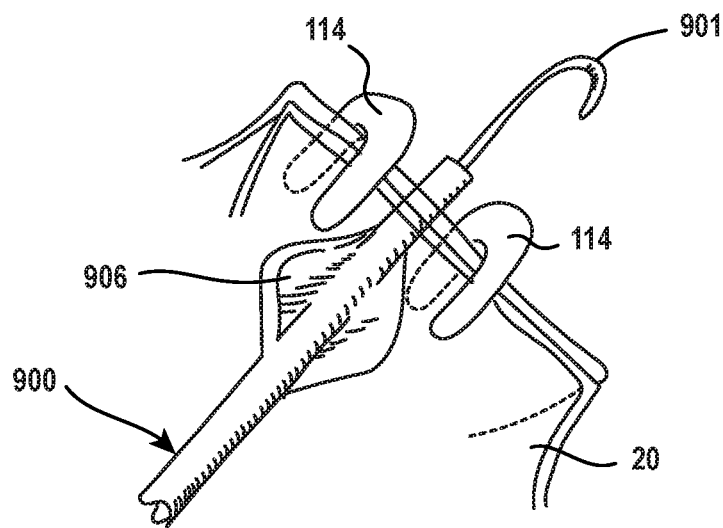
FIG. 14 illustrates an embodiment of a self-centering delivery catheter and/or sizer having a pair of fins for aligning the delivery catheter with cardiac valve anatomy.
Figure 15A:
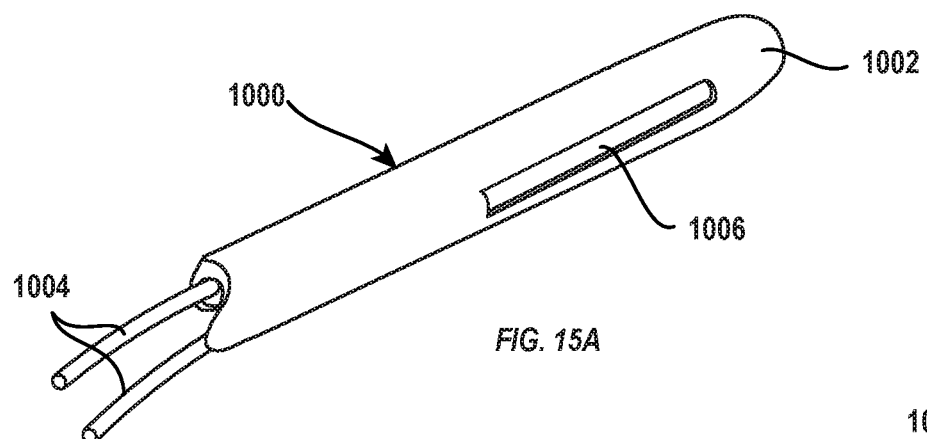
FIGS. 15A and 15B illustrate another embodiment of a self-centering delivery catheter having adjustable-width fins.
Figure 15B:
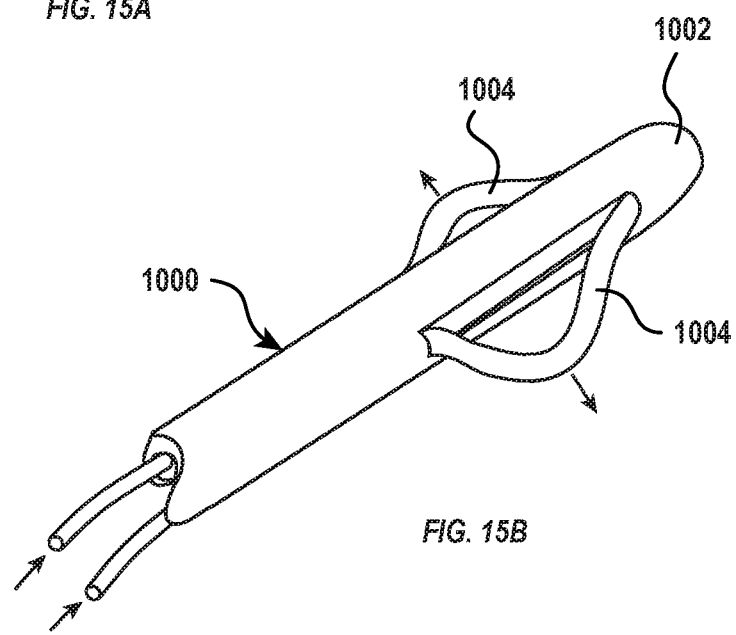

FIGS. 14 through 15B illustrate exemplary embodiments of delivery catheters having a self-centering feature that provides desired alignment to the cardiac valve anatomy. As shown in FIG. 14, a delivery catheter 900 includes a pair of fins 906 extending laterally from the longitudinal axis of the delivery catheter 900 (the leaflets of the mitral valve 20 are shown here as transparent to better illustrate the delivery catheter 900). The fins 906 are positioned near the distal end of the delivery catheter 900 so that when the distal end of the delivery catheter 900 is positioned at the targeted gap, the fins 906 will cause the delivery catheter 900 to rotate as needed to align with the line of coaptation of the mitral valve 20.

For example, if the projected fins 906 are not aligned to the line of coaptation during the approach to the mitral valve 20, the fins 906 will abut against the atrial facing surfaces of the leaflets. Because the leaflets slope closer to each other in the ventricular direction toward the leaflet edges, further movement of the delivery catheter 900 in the ventricular direction will cause the delivery catheter 900 to rotate so that the fins 906 will better fit within the wedge shape of the leaflets. The delivery catheter 900 may travel over a previously positioned guidewire 901, as shown.

The self-centering feature can beneficially ensure that an interventional device passed through the delivery catheter 900 is properly aligned to the line of coaptation of the valve 20. For example, the interventional device carried within the delivery catheter 900 may be rotationally keyed to the delivery catheter such that by ensuring alignment of the delivery catheter 900 also ensures alignment of the interventional device.

The fins 906 are shown here in a symmetric arrangement with each opposing fin having a substantially equal width. When used, such an embodiment will operate to position the distal end of the delivery catheter 900 at the center of the targeted gap (e.g., between the two implanted clips 114). Alternative embodiments may have fins with a non-symmetric arrangement to offset from the center of the gap the position the distal end of the catheter. Such an offset, non-symmetric embodiment may be used where particular patient anatomy and/or procedural requirements require deployment of an interventional device off from the center of a targeted gap.

FIGS. 15A and 15B illustrate an embodiment of a delivery catheter 1000 having adjustable-width fins. FIG. 15A shows a distal end 1002 of the delivery catheter 1000 with the fins 1004 in a retracted position. Wires 1004 (or strips, ribbons, or other suitable structures) pass through the interior of the delivery catheter 1000 and are attached near the distal end 1002. A pair of skives 1006 are also included near the distal end 1002. As shown in FIG. 15B, the wires 1004 may be translated distally such that portions extend laterally out of skives 1006. The laterally extended wires 1004 may then function as the self-centering fins which align the delivery catheter 1000 to the line of coaptation when delivered to the cardiac valve. In some embodiments, the distal portion of the delivery catheter 1000 includes a coating of an elastomer material or other suitable material covering at least the skives 1006. In this configuration, the extending wires 1004 which form the fins are covered and there is no gap between the extended wires 1004 and the skives 1006.

The width of the fins is controllable by translating the wires 1004 relative to the body of the delivery catheter 1000. For example, moving the wires 1004 distally will force greater lengths out of the skives 1006 to increase the effective width of the fins. Likewise, retracting the wires 1004 proximally will pull more wire length in through the skives 1006 to shorten the width of the fins. The wires 1004 may extend proximally to a handle and may be operatively coupled to one or more controls so that an operator can control fin adjustment through manipulation at the handle (see, e.g., FIG. 1). In some embodiments, the wires 1004 are independently controllable, and the widths of each opposing fin may be adjusted to a symmetric or non-symmetric configuration.

Although embodiments of FIGS. 14 through 15B are described above in the context of their use as delivery catheters, it will be understood that they may also be utilized as sizers for informing an operator as to the size of the targeted gap. Determining the size of a targeted gap may therefore inform the selection and/or sizing of the interventional device to deploy at the gap. An operator may pass the fins into the targeted gap and use the width of the fins to determine the size of the gap. For example, if real-time monitoring (e.g., via echo/Doppler) confirms that regurgitation is sufficiently reduced while the fins are positioned within the gap, the properly coapted gap will be determined to be about the same width as the fins. When configured as sizers, the sizers need not necessarily also be capable of delivering an interventional device to the targeted gap. In some implementations, a separate sizer or set of sizers may be utilized to determine gap size, and a separate delivery catheter may then be used to delivery an interventional device.

Attachment/Detachment Mechanisms

Figure 16A:
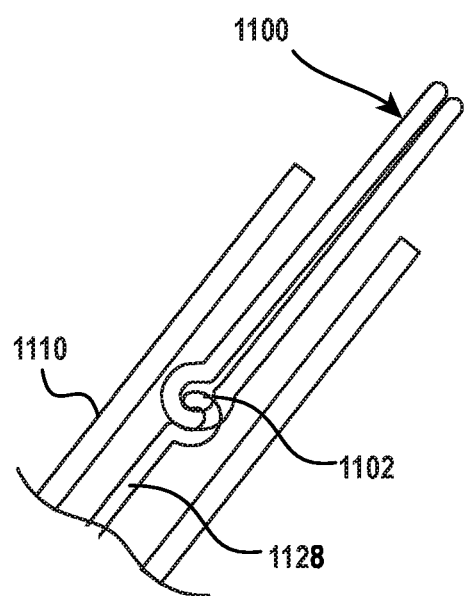
FIGS. 16A through 16C illustrate various embodiments of attachment/detachment mechanisms which may be used with the interventional devices described herein.
Figure 16B:
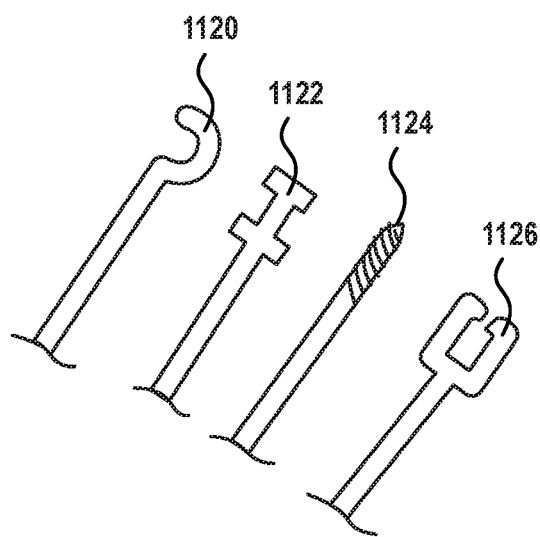
Figure 16C:
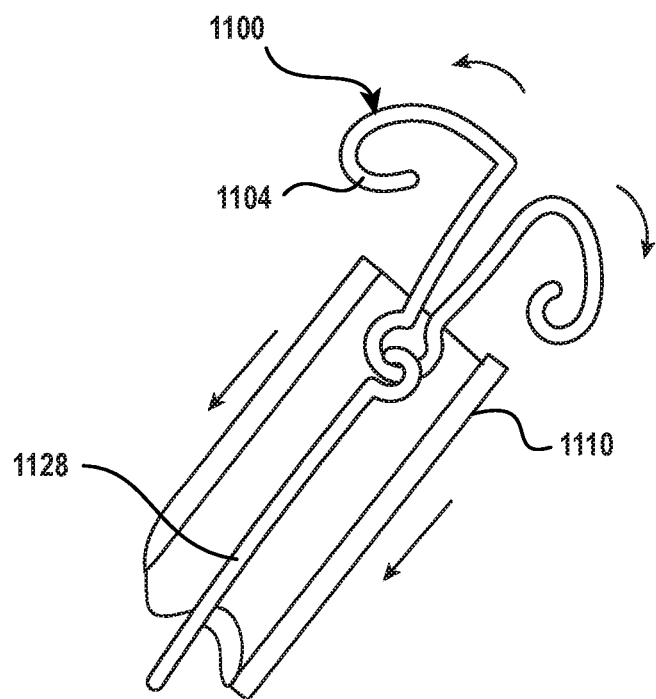

FIGS. 16A through 16C illustrate various exemplary mechanisms for attaching and detaching at least some of the interventional devices described herein. For example, the illustrated interventional device 1100 may generically represent any of the tensioning devices and/or compression devices illustrated in FIGS. 5A through 13D. In FIG. 16A, an interventional device 1100 is shown sheathed within a delivery catheter 1110. An inner member 1128 (formed as a push rod or other suitable structure) couples to the interventional device 1100 at attachment point 1102.

FIG. 16B illustrates various attachment/detachment mechanisms that may be utilized, including a hook member 1120, a fitting member 1122, a threaded member 1124, or a clamp member 1126. The interventional device 1100 is configured so that the attachment point 1102 matches the particular construction of the of the attachment/detachment mechanism of the inner member 1128. Other embodiments may include one or more alternative locking mechanisms suitable for detachably coupling the interventional device 1100 to the inner member 1128. For example, an irreversible shearing feature may be designed to fail at a given stress to detach the inner member 1128 from the interventional device 1100.

FIG. 16C shows retraction of the delivery catheter 1110 relative to the inner member 1128 and resulting unsheathing of the interventional device 1100. Following unsheathing and deployment, the inner member 1128 may be detached from the interventional device 1100 and removed. In preferred embodiments, the delivery catheter 1110 functions as a single outer sheath, however additional (e.g., telescoping) sheaths may be utilized if staged deployment is desired.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be substituted for or combined with elements described in relation to any other embodiment depicted and/or described herein. For example, any of the interventional device embodiments illustrated in FIGS. 5A to 13D may be utilized with any of the delivery catheter or attachment/detachment mechanism embodiments illustrated in FIGS. 14 through 16C.

The invention claimed is:

1. An interventional device for compressing cardiac valve tissue at a targeted gap, the device comprising:
   a distal member having a width defined between opposing side edges;
   a pair of opposing arms each flexibly joined to the distal member along the width, each arm extending proximally from the distal member to a free end, the arms defining an interior space therebetween for holding cardiac valve tissue,
   wherein the arms have a default position, the arms being flexibly moveable apart from one another away from the default position to increase the interior space and to enable receiving cardiac valve tissue within the interior space, further wherein the arms are configured to be biased toward the default position when moved apart from one another, the arms thereby providing a compressive force upon cardiac valve tissue held within the interior space; and
   an anchor coupled to the distal member and extending proximally from the distal member, wherein the anchor extends through the interior space and has a width greater than the width of the distal member,
   wherein the device is detachable from a delivery device for implant to cardiac valve tissue.

2. The interventional device of claim 1, wherein the device is configured in size and shape for deployment at a targeted gap measuring about 2 to 8 mm.

3. The interventional device of claim 1, further comprising a plurality of frictional elements configured to engage with the cardiac valve tissue held within the interior space, the frictional elements being disposed on an interior side of one or both of the arms.

4. The interventional device of claim 1, wherein one or both of the free ends flare outwardly.

5. The interventional device of claim 1, further comprising a neck section joining the distal member to the arms, the neck section being configured as a flexible living hinge from which the arms can flex.

6. The interventional device of claim 1, further comprising an attachment point at the distal member for attaching to the delivery device.

7. The interventional device of claim 1, wherein the width of the anchor is greater than a width of the arms.

8. The interventional device of claim 7, wherein the anchor includes a textured surface configured to encourage tissue ingrowth.

9. The interventional device of claim 7, wherein the anchor has a width of about 5 to 8 mm.

10. An interventional system for compressing cardiac valve leaflet tissue at a targeted gap of a cardiac valve, the system comprising:
an interventional tissue compression device, the compression device comprising:
a distal member having a width defined between opposing side edges,
a pair of opposing arms each flexibly joined to the distal member along the width, each arm extending proximally from the distal member to a free end, the arms defining an interior space between the arms for holding leaflet tissue,
wherein the arms have a default position, the arms being flexibly moveable apart from one another away from the default position to increase the interior space and to enable receiving leaflet tissue within the interior space, and further wherein the arms are configured to be biased toward the default position when moved apart from one another, the arms thereby providing a compressive force upon leaflet tissue held within the interior space, and
an anchor coupled to the distal member and extending proximally from the distal member, wherein the anchor extends through the interior space and has a width greater than the width of the distal member; and
a self-centering delivery catheter, the delivery catheter including a pair of laterally extending fins extending from a distal section of the delivery catheter, the fins enabling alignment of the delivery catheter with a line of coaptation at the targeted gap,
wherein the compression device is detachable from the delivery catheter for implant to the leaflet tissue.

11. The system of claim 10, wherein the fins are configured to be intra-procedurally adjustable in width.

12. The system of claim 11, wherein the distal section of the delivery catheter includes a pair of skives and a corresponding pair of wires laterally extendable through the skives to form the fins.

13. The system of claim 12, wherein the wires extend through a lumen of the delivery catheter such that width of the fins is controllable via translation of the wires.

14. A method of reducing regurgitation through a cardiac valve by compressing leaflet tissue at a targeted gap of the cardiac valve, the method comprising:
delivering an interventional tissue compression device to the targeted gap, the compression device comprising:
a distal member having a width defined between opposing side edges; and
a pair of opposing arms each flexibly joined to the distal member along the width, each arm extending proximally from the distal member to a free end, the arms defining an interior space between the arms for holding leaflet tissue,
wherein the arms have a default position, the arms being flexibly moveable apart from one another away from the default position to increase the interior space and to enable receiving leaflet tissue within the interior space, and further wherein the arms are configured to be biased toward the default position when moved apart from one another, the arms thereby providing a compressive force upon leaflet tissue held within the interior space, and
an anchor coupled to the distal member and extending proximally from the distal member, wherein the anchor extends through the interior space and has a width greater than the width of the distal member; and
deploying the compression device as an implant at the targeted gap to compress the leaflet tissue and reduce regurgitant flow through the targeted gap.

15. The method of claim 14, wherein the targeted gap is at a mitral valve.

16. The method of claim 15, wherein the targeted gap is disposed between two previously deployed implants or between a previously deployed implant and a valve commissure.

17. The method of claim 15, wherein the compression device is delivered to the ventricular side of the mitral valve, and then is retracted proximally to enable the arms to grasp the leaflet tissue at the ventricular side of the mitral valve.

* * * * *